United States Patent
Chehab et al.

(10) Patent No.: US 7,798,640 B2
(45) Date of Patent: Sep. 21, 2010

(54) OPHTHALMIC LENSES USEFUL FOR THE CORRECTION OF PRESBYOPIA WHICH INCORPORATE HIGH ORDER ABERRATION CORRECTION

(75) Inventors: Khaled Chehab, Jacksonville, FL (US); Michael J. Collins, Jollys Lookout (AU); Jeffrey H. Roffman, Jacksonville, FL (US); Ross J. Franklin, Chapel Hill (AU); Brett A. Davis, Holland Park West (AU); Xu Cheng, Jacksonville, FL (US)

(73) Assignee: Johnson & Johnson Vision Care, Inc., Jacksonville, FL (US)

( * ) Notice: Subject to any disclaimer, the term of this patent is extended or adjusted under 35 U.S.C. 154(b) by 806 days.

(21) Appl. No.: 11/550,965

(22) Filed: Oct. 19, 2006

(65) Prior Publication Data
US 2007/0097318 A1    May 3, 2007

(51) Int. Cl.
*A61B 3/10*    (2006.01)

(52) U.S. Cl. .............. 351/205; 351/211; 351/216
(58) Field of Classification Search ............. 351/205, 351/206, 211, 216, 221, 222
See application file for complete search history.

(56) References Cited

U.S. PATENT DOCUMENTS

| 6,554,425 | B1 * | 4/2003 | Roffman et al. ............. 351/177 |
| 2005/0099595 | A1 | 5/2005 | Lindacher et al. |

FOREIGN PATENT DOCUMENTS

| WO | WO 91/09336 | 6/1991 |
| WO | WO 02/32297 A2 | 4/2002 |
| WO | WO 03/032825 | 4/2003 |

\* cited by examiner

*Primary Examiner*—Ricky L Mack
*Assistant Examiner*—Brandi N Thomas
(74) *Attorney, Agent, or Firm*—Todd Volyn

(57) ABSTRACT

The invention provides methods for designing ophthalmic lenses, and lenses produced by this method, which lenses corrects both low order and high order wavefront aberrations of the lens wearer's eyes.

6 Claims, No Drawings

OPHTHALMIC LENSES USEFUL FOR THE CORRECTION OF PRESBYOPIA WHICH INCORPORATE HIGH ORDER ABERRATION CORRECTION

FIELD OF THE INVENTION

The invention relates to ophthalmic lenses that correct presbyopia. In particular, the invention provides presbyopia correcting lenses that correct for the wearer's basic refractive error as well as the wearer's high order optical aberrations.

BACKGROUND OF THE INVENTION

As an individual ages, the eye is less able to accommodate, or bend the natural lens, to focus on objects that are relatively near to the observer. This condition is known as presbyopia. Similarly, for persons who have had their natural lens removed and an intraocular lens inserted as a replacement, the ability to accommodate is absent.

Any number of lens designs have been used in attempt to correct for the wearer's presbyopia. Among the known designs are bifocal and progressive spectacle lenses. Additionally, multifocal contact and intraocular lenses and monovision contact lenses are known.

Monovision contact lenses provide one lens that corrects the wearer's distance vision acuity and that is worn on the dominant eye or eye that predominates for the individuals' distance vision. Additionally, a second lens that corrects the wearer's near vision acuity and is worn on the non-dominant eye is provided. These lenses are disadvantageous because they only correct for low order optical aberrations, such as defocus and astigmatism, leaving the lens wearer's higher order aberrations uncorrected.

DETAILED DESCRIPTION OF THE INVENTION AND PREFERRED EMBODIMENTS

The invention provides methods for designing ophthalmic lenses, and lenses produced by the methods, which lenses corrects both low order and high order wavefront aberrations of the lens wearer's eyes. The lenses produced by the methods of the invention are advantageous in that they provide improved binocular vision, increased depth of focus and improved contrast to the wearer compared to conventional contact lenses used for presbyopia correction.

In one embodiment, the invention provides a method for producing a pair of ophthalmic lenses for an individual comprising, consisting essentially of, and consisting of the steps of: a.) measuring a first basic refractive prescription of a dominant eye of the individual by providing at least one far fixation target; b.) measuring a second basic refractive prescription of a non-dominant eye of the individual by providing at least one far fixation target and measuring a near refractive prescription of the non-dominant eye by providing at least one near fixation target; c.) measuring a first set of high order wavefront aberrations of the dominant eye by providing at least one far fixation target; d.) measuring a second set of high order wavefront aberrations of the non-dominant eye by providing at least one near fixation target; e.) converting each of the first and second sets of high order wavefront aberration measurements to a height difference; and f.) using the first basic refractive prescription and height difference for the dominant eye to provide a first ophthalmic lens and the second basic refractive prescription, near refractive prescription, and height difference for the non-dominant eye to provide a second ophthalmic lens.

By "lens" is meant a spectacle lens, a contact lens, an intraocular lens, a corneal implant lens, an onlay lens, and the like, or combinations thereof. Preferably, the lenses of the invention are contact lenses.

By "basic refractive prescription" is meant the distance power necessary to correct the distance vision acuity and any cylinder power necessary to correct astigmatism.

By "near refractive prescription" is meant the near, or add, power necessary to correct the near visual acuity.

By "dominant eye" is meant the eye that predominates for distance vision.

By "far fixation target" is meant a visual target provided at about 15 feet or more from an individual's eye. By "near fixation target" is meant a visual target at about 30 to about 50 cm from an individual's eye.

In the first step of the invention, a first and a second basic refractive prescription of the lens wearer is measured for an individual's dominant and non-dominant eye, respectively, using at least one far fixation target. Any conventional method may be used for such measurement including, without limitation, use of a phoropter, an autorefractor, trial case lenses, or the like. Alternatively, the measurement may be carried out by ocular wavefront analysis.

In another step of the invention, a near refractive prescription is measured for the individual's non-dominant eye using at least one near fixation target. Any conventional method may be used for such measurement including, without limitation, use of a phoropter, an autorefractor, trial case lenses, or the like. Alternatively, the measurement may be carried out using a modified wavefront aberrometer capable of providing near fixation targets.

In yet another step of the method of the invention, the high order wavefront aberrations of each of the individual's dominant eye and non-dominant eye are measured at a far fixation target. By "high order wavefront aberrations" is meant wavefront aberrations other than low order sphere and cylinder. By "wavefront aberrations" is meant the difference between the wavefront for spherical aberration, astigmatism, coma, and other distortions emerging from the eye compared to a plane wavefront emerging from the eye or a perfect spherical wavefront converging on the retina. In the method of the invention, the high order wavefront measurement for the dominant eye is carried out by providing the lens wearer at least one far fixation target. The high order wavefront aberrations for the individual's non-dominant eye is measured at at least one near fixation target.

Apparatuses for performing the aberration measurements include, without limitation, aberroscopes, devices that measure ocular Modulation Transfer Function by point spread or line spread, or any similar devices that measure, estimate, interpolate, or calculate the ocular optical wavefront. An aberroscope capable of measuring the distance vision target is available from Wavefront Sciences, Inc, Albuquerque, N. Mex. It is well known in the art how to utilize such an aberroscope, as well as other devices available for aberration measurement, to measure targets at near distances.

Once obtained, each of the aberration measurements then may be mathematically converted to a height difference thus providing an elevation map above and below a designated mean sphere value, known as the optical path difference. Correction for the aberrations will be provided by introduction into the lens design of an optical path difference, or aberration inverse filter, that offsets the distortions due to the ocular aberrations.

The height differences, along with the basic refractive prescription, and optionally corneal topographic data, are then used to provide a lens for the wearer. The data may be transformed onto a grid pattern of a rectilinear, polar concentric, or spiral format to correspond to the mechanism by which the surface of a lens or lens mold may be tooled using a computer numeric controlled ("CNC") lathe, direct machining of a polymer button, milling, laser ablation, injection molded insert or the like or a combination thereof. The required changes in the lens' surface elevation or slope to achieve correction of the aberrations may be incorporated onto the lens' front surface, back surface, or a combination thereof.

In one embodiment of the invention, either the front, or convex, or the back, or concave, surface of the lens incorporates the basic refractive prescription of the lens wearer and, in the case of the non-dominant eye lens, also incorporates the near refractive prescription. The opposite surface of the lens contains an optic zone that corrects the lens wearer's high order wavefront aberrations. In an alternative embodiment and preferably, either or both of the basic refractive prescriptions and aberration correction may be divided between the front and back surfaces of the dominant eye lens and the basic refractive prescription, near refractive prescriptions, and aberration correction similarly may be divided between the surfaces of the non-dominant eye lens. As yet another embodiment, the entirety of the refractive prescriptions and aberration correction may be either on the front or back surface of the lens. If corneal topography data is incorporated into the lens design, preferably all of the refractive prescription and aberration correction is on the front surface and the topographic data is used in the design of the back surface.

For the contact lenses of the invention, in those embodiments in which both basic refractive and near refractive power are provided in the form of annular zones, the basic refractive power annular zones preferably alternate with the near refractive power annular zones. Additionally, cylinder power, prism power or both may be combined with either or both of the basic and near refractive powers.

In those case in which both near and basic refractive power annular zones are used in the contact lens for the dominant eye, the ratio of the lens' optic zone area devoted to the basic and near refractive powers must be such that more area is devoted to the distance power. For the lens of the non-dominant eye, more lens area will be devoted to the near power. The preferred areas, on a percentage basis, for both the dominant and non-dominant eye lenses are disclosed in U.S. Pat. Nos. 5,835,192, 5,485,228, and 5,448,312.

In another embodiment, the invention provides a method for producing a pair of ophthalmic lenses for an individual comprising, consisting essentially of, and consisting of the steps of: a.) measuring a first basic refractive prescription of a dominant eye of the individual by providing at least one far fixation target; b.) measuring a second basic refractive prescription of a non-dominant eye of the individual by providing at least one far fixation target and measuring a near refractive prescription of the non-dominant eye by providing at least one near fixation target; c.) measuring a first set of high order wavefront aberrations of the dominant eye by providing at least one far fixation target; d.) measuring a second set of high order wavefront aberrations of the non-dominant eye by providing at least one far fixation target and measuring a third set of high order wavefront aberrations of the non-dominant eye by providing at least one near fixation target; e.) converting the first set of high order wavefront aberration measurements to a first height difference; f.) calculating an average measurement of the second and third sets of measured high order wavefront aberrations and converting the average measurement to a second height difference and g.) using the first basic refractive prescription and first height difference for the dominant eye to provide a first ophthalmic lens and the second basic refractive prescription, near refractive prescription, and second height difference for the non-dominant eye to provide a second ophthalmic lens. In yet another embodiment of the invention, the high order wavefront aberrations may be measured at a near and far fixation target for both of the dominant and non-dominant eye and, for each eye, the average of these wavefronts may be calculated. In still another embodiment, the high order wavefront aberrations are measured at a near and far fixation target for both of the dominant and non-dominant eye and, for each eye, the average of these wavefronts may be calculated, but the near refractive prescription is not measured for the non-dominant eye.

In any of these embodiments, the calculation of the average measurement may be carried out by any convenient method. For example, the calculation may be provided by calculating an average of Zernike terms, a weighted average of Zernike terms, or an exponentially weighted average of Zernike terms. Alternatively, the average may be calculated by optimization of image quality metrics, minimization of total wavefront RMS, selective minimization of selected waverfront terms, optimization of the PSF one-half bandwidth, or optimization of any of the Visual Strehl ratios, MTFs or OTFs.

In still other embodiments of the lenses of the invention, the back surface of one or both of the lenses is matched to the wearer's corneal topography. For lenses incorporating an inverse topographic elevation map of the lens wearers' cornea, the corneal topography may be determined by any known method including, without limitation, by use of a corneal topographer. For soft contact lens manufacture, the elevational data initially is applied to a lens model in the unflexed state. Next, the data is transformed by taking into account the soft lens flexure, or wrap, when the lens placed on the eye. Thus, the effects of both elevation of the cornea and wrap are accounted for when using the corneal topographic data. The flexure transformed data then may be mapped onto a CNC grid pattern and used to make the lenses or mold tool surface.

Contact lenses useful in the invention may be either hard or soft lenses. Soft contact lenses, made of any material suitable for producing such lenses, preferably are used. The lenses of the invention may have any of a variety of corrective optical characteristics incorporated onto the surfaces in addition to aberration correction and distance and near optical powers, such as, for example, cylinder power.

The contact lenses of the invention may be formed by any conventional method. For example, the annular zones formed therein may produced by diamond-turning using alternating radii. The zones may be diamond-turned into the molds that are used to form the lens of the invention. Subsequently, a suitable liquid resin is placed between the molds followed by compression and curing of the resin to form the lenses of the invention. Alternatively, the zones may be diamond-turned into lens buttons.

In another embodiment, the correction above-described is provided on each lens of a spectacle lens pair. The spectacle lenses may be formed by any known method including, without limitation, grinding of a lens blank, casting, molding, or combinations thereof. In a preferred embodiment, an optical preform having some or all of the basic refractive prescription for the dominant eye and basic and near refractive prescription for the non-dominant eye is used and one or more surfaces are cast onto the optical preform to provide aberration correction and, optionally, additional basic refractive prescription power.

What is claimed is:

1. A method for producing a pair of ophthalmic lenses for an individual, comprising of the steps of:

a.) measuring a first basic refractive prescription of a dominant eye of the individual by providing at least one far fixation target;

b.) measuring a second basic refractive prescription a non-dominant eye of the individual by providing at least one far fixation target and measuring a near refractive prescription of the non-dominant eye by providing at least one near fixation target;

c.) measuring a first set of high order wavefront aberrations of the dominant eye by providing at least one far fixation target;

d.) measuring a second set of high order wavefront aberrations of the non-dominant eye by providing at least one far fixation target and measuring a third set of high order wavefront aberrations of the non-dominant eye by providing at least one near fixation target;

e.) converting each of the first set of high order wavefront aberration measurements to a first height difference;

f.) calculating an average measurement of the second and third sets of measured high order wavefront aberrations and converting the average measurement to a second height difference; and g.) using the first basic refractive prescription and first height difference for the dominant eye to provide a first ophthalmic lens and the second basic refractive prescription, near refractive prescription, and second height difference for the non-dominant eye to provide a second ophthalmic lens.

2. A lens produced according to the method of claim 1.

3. A method for producing a pair of ophthalmic lenses for an individual, comprising the steps of:

a.) measuring a first basic refractive prescription of a dominant eye of the individual by providing at least one far fixation target;

b.) measuring a second basic refractive prescription of a non-dominant eye of the individual by providing at least one far fixation target and measuring a near refractive prescription of the non-dominant eye by providing at least one near fixation target;

c.) measuring a first set of high order wavefront aberrations of the dominant eye by providing at least one far fixation target and a second set of high order wavefront aberrations by providing at least one near fixation target;

d.) calculating an average of the first and second set of wavefront aberration measurements;

e.) converting the average wavefront aberration calculated in step d, to a first height difference f.) measuring a third set of high order wavefront aberrations of the non-dominant eye by providing at least one far fixation target and a fourth set of high order wavefront aberrations of the non-dominant eye by providing at least one near fixation target;

g.) calculating an average of the third and fourth set of wavefront aberration measurements;

h.) converting the average wavefront aberration calculated in step f, to a second height difference; and i.) using the first basic refractive prescription and first height difference for the dominant eye to provide a first ophthalmic lens and the second basic refractive prescription, near refractive prescription, and second height difference for the non-dominant eye to provide a second ophthalmic lens.

4. A lens produced according to the method of claim 3.

5. A method for producing a pair of ophthalmic lenses for an individual, comprising the steps of:

a.) measuring a first basic refractive prescription of a dominant eye of the individual by providing at least one far fixation target;

b.) measuring a second basic refractive prescription of a non-dominant eye of the individual by providing at least one far fixation target;

c.) measuring a first set of high order wavefront aberrations of the dominant eye by providing at least one far fixation target and a second set of high order wavefront aberrations by providing at least one near fixation target;

d.) calculating an average of the first and second set of wavefront aberration measurements;

e.) converting the average wavefront aberration calculated in step d, to a first height difference;

f.) measuring a third set of high order wavefront aberrations of the non-dominant eye by providing at least one far fixation target and a fourth set of high order wavefront aberrations of the non-dominant eye by providing at least one near fixation target;

g.) calculating an average of the third and fourth set of wavefront aberration measurements;

h.) converting the average wavefront aberration calculated in step f, to a second height difference; and i.) using the first basic refractive prescription and first height difference for the dominant eye to provide a first ophthalmic lens and the second basic refractive prescription and second height difference for the non-dominant eye to provide a second ophthalmic lens.

6. A lens produced according to the method of claim 5.

* * * * *